(12) United States Patent
Johansson et al.

(10) Patent No.: US 6,258,997 B1
(45) Date of Patent: Jul. 10, 2001

(54) LIQUID-PERVIOUS COVER LAYER FOR AN ABSORBENT ARTICLE

(75) Inventors: Anette Johansson; Nils Ljungqvist, both of Gothenburg (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/367,814

(22) PCT Filed: Feb. 19, 1998

(86) PCT No.: PCT/SE98/00292

§ 371 Date: Sep. 30, 1999

§ 102(e) Date: Sep. 30, 1999

(87) PCT Pub. No.: WO98/36721

PCT Pub. Date: Aug. 27, 1998

(30) Foreign Application Priority Data

Feb. 21, 1997 (SE) .................................... 9700606

(51) Int. Cl.⁷ ........................................ A61F 13/15
(52) U.S. Cl. .............. 604/378; 604/385.03; 604/385.23; 604/385.01; 604/387
(58) Field of Search ................. 604/354, 385.03, 604/385.23, 385.01, 384, 364, 367, 365, 387, 378

(56) References Cited

U.S. PATENT DOCUMENTS

| | | | |
|---|---|---|---|
| 3,967,623 | * | 7/1976 | Butterworth et al. ............... 128/287 |
| 4,054,141 | * | 10/1977 | Schwaiger et al. .................. 128/287 |
| 4,826,498 | * | 5/1989 | Koczab ................................ 604/383 |
| 5,002,814 | * | 3/1991 | Knack et al. .......................... 428/85 |
| 5,069,677 | * | 12/1991 | Sakurai et al. ...................... 604/370 |
| 5,470,326 | * | 11/1995 | Dabi et al. ........................... 604/383 |
| 5,514,120 | * | 5/1996 | Johnston et al. .................... 604/378 |
| 5,843,064 | * | 12/1998 | Koczab ................................ 604/378 |
| 5,885,268 | * | 3/1999 | Bien et al. ........................ 604/385.1 |

FOREIGN PATENT DOCUMENTS

| | | | |
|---|---|---|---|
| 1007041 | 2/1995 | (BE) . | |
| 0 737 462 A1 | * | 4/1995 | (EP) ..................................... 604/378 |
| 0 737 462 | 10/1996 | (EP) . | |
| WO 97/00656 | 1/1997 | (WO) . | |

* cited by examiner

*Primary Examiner*—Aaron J. Lewis
*Assistant Examiner*—Paul Shanoski
(74) *Attorney, Agent, or Firm*—Young & Thompson

(57) ABSTRACT

A liquid-pervious cover layer for an absorbent article, such as a sanitary napkin, a panty-liner, a diaper, or the like, which comprises a liquid-pervious carrier layer against which individual hydrophobic fibers, detached from each other and each exhibiting two fiber ends, are attached with one fiber end against the carrier layer, with an attachment angle α between the carrier layer and each individual fiber. The cover layer exhibits fiber-free regions for facilitating liquid transfer through the cover layer. The invention further includes an absorbent article provided with the cover layer, and a method of manufacturing the cover layer.

19 Claims, 2 Drawing Sheets

LIQUID-PERVIOUS COVER LAYER FOR AN ABSORBENT ARTICLE

CROSS REFERENCE TO RELATED APPLICATION

This is the 35 USC 371 national stage of International application PCT/SE98/00292 filed on Feb. 19, 1998, which designated the United States of America.

TECHNICAL FIELD

The invention pertains to a liquid pervious cover layer for an absorbent article such as a diaper, an incontinence protector, a sanitary napkin or the like, which exhibits a liquid-pervious carrier layer having a first surface and a second surface, wherein the first surface of the carrier layer exhibits a multitude of individually arranged fibres, each fibre exhibiting a first fibre end and a second fibre end, and being attached with one fibre end against the first surface of the carrier layer. The invention also relates to an absorbent article provided with the cover layer and to a method for manufacturing of the cover layer.

TECHNICAL BACKGROUND

High demands on both softness and dryness are made on liquid-pervious cover layers for absorbent articles of this type, which are intended to bear on the body of the user during use.

However, it has proved to be difficult to achieve a liquid-pervious cover layer with a soft and textile-like surface which at the same time remains dry during use.

One problem, when using nonwoven materials or other similar textile materials as liquid-pervious cover layers for absorbent articles, is that the fibre structure of the material absorbs liquid when the cover layer is wetted. A certain amount of the liquid is not conducted downwards to the underlying absorbent structure, but remains in the liquid-pervious cover layer instead. Since the liquid-pervious cover layer bears on the body of the user during use, such articles are perceived as being wet and uncomfortable to wear already after an initial wetting.

Furthermore, the wet surface, which is in direct contact with the skin during use, leads to an increased risk of skin irritations and infections.

The most important reason for some of the liquid remaining in the fibre structure is that textile materials usually consist of an irregular fibre structure with fibres or fibre filaments oriented in the plane of the material. This implies that excreted body fluid, by means of the capillary action of the fibres, is distributed along the fibre structure in the direction of the material plane. Also liquid which is not absorbed into the fibre capillaries is conducted along the fibre structure in the direction of the material plane, and is collected in cavities between the fibres in which the liquid is retained without being able to spread further to underlying material. These factors result in a certain amount of liquid remaining in the cover layer and causing a wet surface closest to the user.

Another problem with the nonwoven materials of today, having fibres substantially oriented in parallel with the material plane, is that the possibility to control the wetting course by means of utilizing the properties of the fibres, such as for example the wettability of different fibres, is limited. Furthermore, the possibility to control the wetting course is limited when it comes to the location of the fibres and their design.

It is previously known from U.S. Pat. No. 3,967,623 to use a liquid-pervious cover layer, consisting of a perforated plastic layer, as a carrier material onto which fibres treated with wetting agent are applied in order to create a soft and fluffy surface. The individual fibres are oriented so that they are directed upwards towards the user during use and are approximately 5 mm long. Since the fibres are directed upwards towards the user, a soft and fluffy surface is created. However, the problem remains that the liquid transfer from the fibres to the underlying absorbent body inside is poor, which results in the surface closest to the user remaining wet after wetting.

BE 09300552 relates to a cover layer for an absorbent article, which cover layer consists of a plastic film which at least on one side is covered by fibres which are attached at an angle to the plastic film. In order to obtain such a structure, the fibres may, for example by means of flocking, be attached with one of their fibre ends against a fused fibre fixation layer on the plastic film. The plastic film may be perforated so that the material becomes liquid-pervious. The fibres are 0.3 to 2.5 mm long and the thickness may be varied with regard to how soft the layer should be. Different fibres may be used, such as for example viscose, cotton, polyethylene, polypropylene, polyester and polyamide.

The risk of the liquid spreading in the plane of the material and thereby along the surface of the cover layer is minimal with this previously known cover layer. Furthermore, the cover layer exhibits a soft surface closest to the user. With this previously known cover layer, however, the problem of achieving a dry surface, when the layer is used as a liquid-pervious surface material on an absorbent article, still remains.

SUMMARY OF THE INVENTION

By means of the present invention, the problems with achieving a liquid-pervious cover layer for absorbent articles, which is soft and exhibits a dry surface also after wetting, has essentially been eliminated.

Accordingly, by means of the invention, a soft, skin-friendly and textile-like cover layer for an absorbent article has been achieved, which layer has the ability to conduct liquid downwards to an underlying absorbent structure and to thereby maintain a dry surface closest to the user.

A liquid-pervious cover layer according to the invention is primarily distinguished by that the carrier layer exhibits a plurality of regions which are substantially free from fibres and which each occupies a surface such that a circle having a diameter of 3 to 15 mm and preferably having a diameter of 3 to 10 mm can be accommodated within each fibre-free region.

The fibre-free regions of the cover layer allow liquid to pass between the hydrophobic fibres, through the liquid pervious cover layer. At the same time, the hydrophobic fibres provide a soft, skin-friendly surface, isolating absorbed liquid from the user's skin when the cover layer is being used as a liquid-pervious topsheet on an absorbent article.

A cover layer in accordance with the invention has been found to perform particularly well when the hydrophobic fibres are 0.3–2.5 mm long and preferably 0.3–1.5 mm long.

The fibres can be arranged in a wide variety of different surface patterns such as squares, bands, stars, flowers, dots, rings, etc. Mixed patterns and patterns having varying fibre densities can also be used. When the fibres are arranged in stripes or band-shaped regions, the distance between two neighboring fibre-covered regions should be in the order of 3–15 mm and preferably 3–10 mm.

In order to achieve the desired liquid-permeability, it has been shown that the total area of the fibre-free regions should occupy at least 25% of the surface of the carrier layer. However, the fibre-free regions should not occupy more than 60% and preferably not more than 50% of the surface.

The advantage with such a cover layer is that the hydrophobic surface of the individual fibres creates a dry barrier between the liquid-pervious carrier layer and the user. This implies that the risk that the surface bearing most closely on the user is perceived as wet after wetting is reduced.

According to the invention, the individual fibres are attached only to delimited regions of the total area of the carrier layer, while other regions of the surface of the carrier layer thus are left free from individual fibres. For instance, the individual fibres can be attached in a row pattern along the longitudinal direction of the article. The advantage with such a pattern is that the liquid is distributed from the wetting point in a direction towards the end portions of the article, whereas liquid spreading in the lateral direction is counteracted. Thereby, the risk of the region around the wetting point being saturated with liquid, with leakage in a lateral direction as a consequence, is reduced. A further advantage, with liquid distribution from the wetting point of the article to the end portions of the article, is that the liquid distribution in an underlying absorbent structure becomes more uniform. This results in a better utilization of the total liquid absorption capacity of the underlying structure. The individual fibres may also be attached in other patterns, wherein the carrier surface exhibits delimited regions which are free from attached fibres.

The carrier layer may further exhibit a continuous region across the entire surface of the carrier layer which is free from fibres. This implies that the individual fibres are attached to delimited smaller regions of the surface of the carrier layer, which regions are delimited from each other by the continuous region of the carrier layer which is free from fibres. An advantage with such an embodiment is that the liquid distributing ability of the carrier layer is increased, since the liquid is more easily distributed along a continuous region which is free from attached fibres exhibiting a hydrophobic surface structure. This embodiment is above all advantageous when the carrier layer is constituted of a nonwoven material which in itself can function as a liquid distributing layer, but is of course also applicable for other carrier materials.

According to one embodiment, the individual fibres are constituted of bicomponent fibres, exhibiting a hydrophobic surface and a hydrophilic core. An advantage with using such bicomponent fibres is that the hydrophilic core of the fibres has the ability to conduct the liquid downwards towards the liquid-pervious carrier layer. This implies that the liquid quantity between the fibres decreases, resulting in a drier surface and a reduced risk of liquid leakage out to the underpants of the user.

According to another embodiment, the components in the bicomponent fibre have different melting temperatures. Thereby, the component which constitutes the core of the fibres preferably exhibits a higher melting temperature than the component which constitutes the outer structure of the fibres. The advantage with a difference in melting temperature is that the need for an adhesive, when attaching the fibres to the carrier layer, is eliminated since the fibres are heated to a temperature between the melting temperatures of the fibre components when they are applied against the carrier material. This implies that the outer component melts, whereby the bicomponent fibres exhibit a melted fibre surface which attaches to the carrier layer.

According to still another embodiment, the individual fibres are constituted of hollow fibres, having an outer surface and an inner surface whereof at least the outer surface of the hollow fibre is hydrophobic. Accordingly, the inner surface of the hollow fibre is either hydrophilic or hydrophobic. An advantage with these fibres is that liquid can be conducted via the cavities of the fibres downwards towards the liquid-pervious carrier layer. This implies that the quantity of external liquid between the individual fibres is reduced, resulting in a drier surface and a reduced risk of liquid leakage to the underpants of the user. A further advantage with hollow fibres is that the material consumption during the manufacture of such fibres is small, which results in a low raw material consumption.

According to still another embodiment, the carrier layer is constituted of a multilayered laminate. The multilayered laminate exhibits at least one bottom layer, and a fibre fixation layer, wherein the fibre fixation layer has a lower melting temperature than the bottom layer. When attaching the individual fibres, the carrier layer is heated to such a temperature that the fibre fixation layer melts, whereas the bottom layer is intact. Accordingly, the need for a special adhesive for attaching the fibres is eliminated.

According to still another embodiment, the carrier layer exhibits liquid-penetrability since the layer has been perforated. This embodiment primarily refers to carrier layers which are constituted of an initially liquid-impervious material, such as a film exhibiting one or several layers, but can also be applied in order to increase the liquid-penetrability of different types of nonwoven materials.

The carrier layer may further comprise a liquid-pervious textile material, such as for example a hydrophilic nonwoven. An advantage with a hydrophilic nonwoven as a carrier material is that such materials are liquid-pervious in themselves. This implies that the carrier layer does not have to be perforated in order to achieve liquid-penetrability. A further advantage with a hydrophilic nonwoven as a carrier material is that such a material has the ability to distribute liquid in the plane of the material layer. Accordingly, such a carrier layer also functions as a liquid distributing layer, which results in a higher degree of utilization of the total absorption capacity of the underlying structure.

In still another embodiment, the fibre density varies across the surface of the carrier layer by using different patterns or pattern densities for different parts of the surface. This implies that the liquid-pervious carrier layer exhibits a difference in the number of attached individual fibres per unit of area. The advantage with a difference in fibre density is that the possibility to guide liquid in the desired direction is increased. A varied fibre density may thus reduce the risk of the region around the wetting point being saturated with liquid with leakage as a consequence.

According to one embodiment, the attachment angle $\alpha$, between the carrier layer and each individual fibre is approximately 90°, but may of course vary somewhat between the different fibres. The advantage with such an embodiment is that the body fluid rapidly is conducted in a direction straight into the carrier layer, and further into the underlying absorbent structure. Accordingly, the risk of the layer being perceived as wet is minimized.

According to another embodiment, the angle $\alpha$ between the carrier layer and each individual fibre is 30–70°. Since the fibres are angled so that they exhibit a smaller angle than 90° between the surface of the carrier layer and the individual fibres, the surface maintains a clean and dry visual impression also after use since the oblique fibres disguise the liquid-pervious carrier layer so that this is not visible when the user observes the sanitary napkin from above.

There are several factors influencing the choice of fibres and carrier layers, and the location of the fibres across the surface of the carrier layer. For instance, the properties of the material must be adapted with respect to which type of liquid the article is intended to absorb, and to which properties the underlying absorbent structure exhibits, with regard to liquid drainage ability and liquid retention ability. By means of the possibility to vary the pattern structure, the fibre type and the type of carrier layer within the scope of the invention, however, a liquid-pervious cover layer is achieved, exhibiting a reduced surface wetness and an increased softness.

The invention also includes an absorbent article such as a sanitary napkin, a panty-liner, a diaper, or the like comprising an absorbent body enclosed in a cover, wherein at least a portion of the cover consists of a liquid-pervious cover layer in accordance with the invention. The liquid-pervious cover layer comprises a liquid-pervious carrier layer against which individual hydrophobic fibres, detached from each other and each exhibiting two fibre ends, are attached with one fibre end against the carrier layer. Thereby, an attachment angle a is formed between the carrier layer and each individual fibre. The liquid-pervious cover layer is primarily characterized in that the carrier layer exhibits a plurality of regions which are substantially free from fibres and which each occupies a surface such that a circle having a diameter of 3 to 15 mm and preferably having a diameter of 3 to 10 mm can be accommodated within each fibre-free region.

Furthermore, the invention includes a method of manufacturing a cover layer for an absorbent article wherein individual fibres, each exhibiting a first fibre end and a second fibre end, are applied with the first fibre end against a carrier layer. At least at the first fibre end, the cross-sectional area of the fibres exhibits a first portion primarily consisting of a first component and a second portion primarily consisting of a second component, wherein at least the first component is fusible and exhibits a melting temperature at which the second component occurs in a solid state. Only the first component is caused to melt, either before or after the application of the fibres against the carrier layer. Thereafter, the temperature of the fibres is lowered below the melting temperature of the first component, whereby a solid connection between the fibres and the carrier layer is obtained. The advantage of attaching the fibres to the carrier layer by means of causing the first component to melt is that the need for an adhesive when attaching the fibres to the carrier layer is eliminated. Furthermore, the need for a melted fibre fixation layer is eliminated, which implies that the carrier layer can be constituted of a single material layer.

BRIEF DESCRIPTION OF THE DRAWINGS

In the following, the invention will be described in greater detail with reference to the figures which are shown in the attached drawings.

DETAILED DESCRIPTION OF PREFERRED EMBODIMENTS

Figure 1:
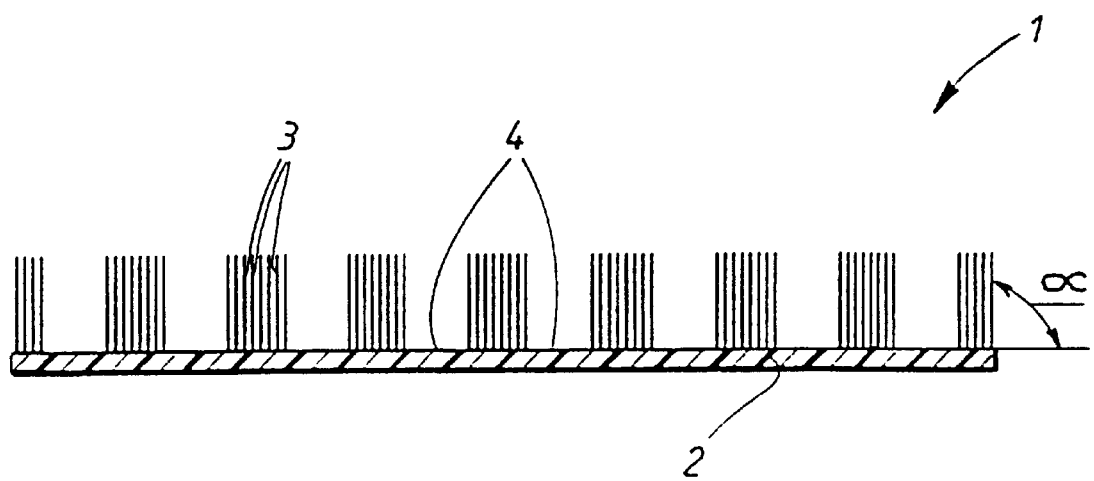
FIG. 1 shows a cross-section through a liquid-pervious cover layer according to the invention.

The liquid-pervious cover layer 1, shown in FIG. 1, consists of a carrier layer 2 onto which individual fibres 3 are attached. The individual fibres 3 are attached to the carrier layer 2 with one end, whereas the other, free end is directed away from the carrier layer, whereby the individual fibres are arranged at an angle α to the carrier layer. In the shown example, the attachment angle α is approximately 90°, but may of course vary somewhat between the different fibres. In order to facilitate liquid passage through the liquid-pervious cover layer 1, the fibres 3 are arranged in spaced-apart regions with fibre-free regions 4 therebetween.

When attaching the fibres 3 to the carrier material 2, the fibres 3 are oriented so that one of the fibre ends is directed towards the carrier layer 2. This fibre orientation is achieved, for instance, by means of flocking. The individual fibres 3 are constituted of fibres comprising a surface which in the main is hydrophobic. Accordingly, the cover structure is constituted of for example a polyolefin. According to one embodiment, the fibres 3 are constituted of bicomponent fibres where the surface component consists of polyethylene, such as for example LDE (low density polyethylene), HDPE (high density polyethylene) or LLDPE (linear low density polyethylene). The fibre surface may further consist of polymeric mixtures comprising at least two of the above-mentioned polyethylene components, or other components exhibiting a substantially hydrophobic surface.

The core of the fibres 3 is constituted of a less hydrophobic material than the surface of the fibres. One example of a material which is less hydrophobic than polyethylene is polyester. Besides the fact that the component is less hydrophobic, polyester also exhibits a higher melting temperature than polyethylene. This difference in melting temperature between the components can be utilized when attaching the fibres to the carrier layer.

Since the fibres are heated to a temperature which is between the melting temperature of the two components during the attachment, a melted surface is formed on the bicomponent fibres, whereas the core remains solid. Thereby, the melted surface component may be utilized for attaching the fibres to the carrier layer 2, resulting in the elimination of the need for a special adhesive for the attachment of the fibres 3 to the carrier layer 2.

The attachment of the fibres 3 to the carrier layer 2 may of course also be accomplished with another attachment method. The bicomponent fibre may further consist of other components than those mentioned above which exhibit a difference in hydrophilicity. The individual fibres 3 can further be constituted of hollow fibres which exhibit a hydrophobic surface and a hollow core. The fibre surface may for example be constituted of polyolefins or other materials exhibiting a hydrophobic surface.

The carrier layer 2 may be a single material layer, or consist of a multilayered laminate. The carrier layer 2 shown in FIG. 1 may be constituted of a single material layer, such as for example a plastic film or a hydrophilic nonwoven.

The individual fibres 3 are attached to the carrier layer 2, for example by means of being applied onto a melted fibre fixation layer, or with an adhesive such as for example hot-melt, hydrophilic glue or any other adhesive which is suitable for the purpose. As mentioned above, the fibres 3 may further be attached to the carrier layer by means of the fibres 3 being constituted of bicomponent fibres comprising components exhibiting different melting temperatures. The fibres 3 may also be attached to the carrier layer by means of the fibres 3 being constituted of bicomponent fibres, comprising components exhibiting different melting temperatures. The fibres 3 may also be attached to the carrier layer 2 by means of the carrier layer 2 consisting of a multilayered laminate comprising a bottom layer and a fibre fixation layer. The bottom layer exhibits a higher melting temperature than the fibre fixation layer and consists of, for example, HDPE, polypropylene or another material suitable for the purpose. The fibre fixation layer consists of for example LDPE, LLDPE, or other materials suitable for the purpose exhibiting a lower melting temperature than the bottom layer material.

Figure 2:
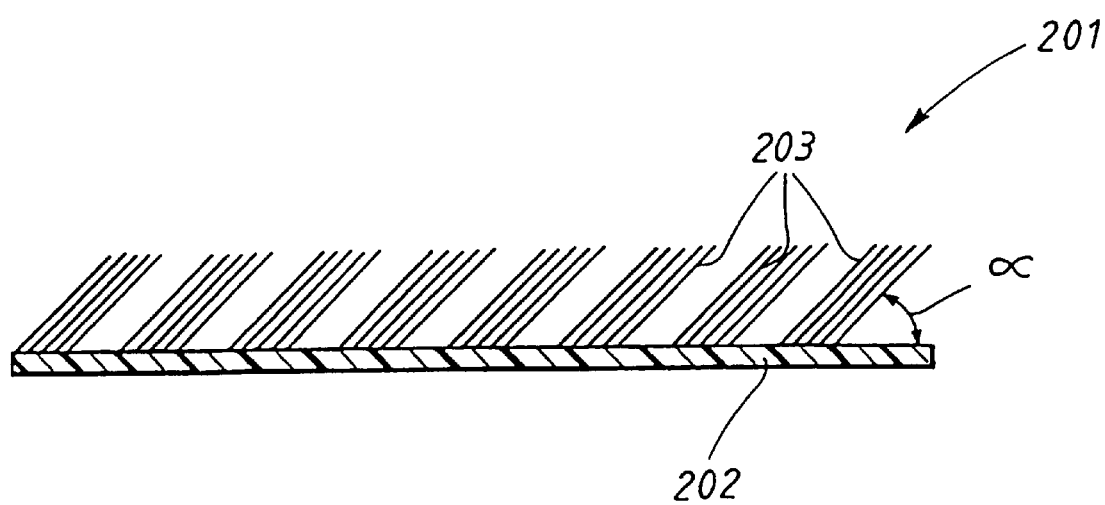
FIG. 2 shows another cross-section through a liquid-pervious cover layer according to the invention and FIG. 3 shows a sanitary napkin according to the invention seen from the side which is intended to be facing the user during use.

The liquid-pervious cover layer 201 shown in FIG. 2 has a similar construction as the liquid-pervious layer 1 shown in FIG. 1. Accordingly, the liquid-pervious layer 201 exhibits a barrier layer 202, such as the carrier layer 2 shown in FIG. 1, onto which fibres 203 are attached. The fibres 203 are attached to limited regions of the total area of the carrier layer 202, whereby the carrier layer 202 exhibits regions which are free from fibres 203. The fibres 203 are attached with one of their ends, whereas the other, free end is directed away from the carrier layer 202, whereby the individual fibres 203 are attached at an angle α to the carrier layer 202. The angle α between the individual fibres 203 and the carrier layer 202 is 30–70°, preferably approximately 45°. Since the individual fibres are angled to the carrier layer 202 with an angle α which is smaller than 90°, this implies that the regions of the carrier layer 202 which are free from fibres 3 are not visible when the liquid-pervious layer 201 is observed from above.

Like the fibres 3, the fibres 203 may be constituted of bicomponent fibres or hollow fibres exhibiting a hydrophobic surface. The carrier layer 202 may be a single material layer, or consist of a multilayered laminate. The carrier layer 202 shown in FIG. 2 is only constituted of one layer, such as for example a plastic film or a hydrophilic nonwoven. The fibres 203 are attached to the carrier layer 202 for example by means of being applied onto a melted fibre fixation layer, or by means of being applied onto an adhesive layer such as for example hot-melt, hydrophilic glue or any other adhesive suitable for the purpose. Furthermore, the fibres 203 may be constituted of bicomponent fibres consisting of a fibre surface with a lower melting temperature than the core of the bicomponent fibres. This implies that the melted surface component of the fibres 203 attaches to the carrier surface and consequently the need for a special adhesive is eliminated.

Figure 3:
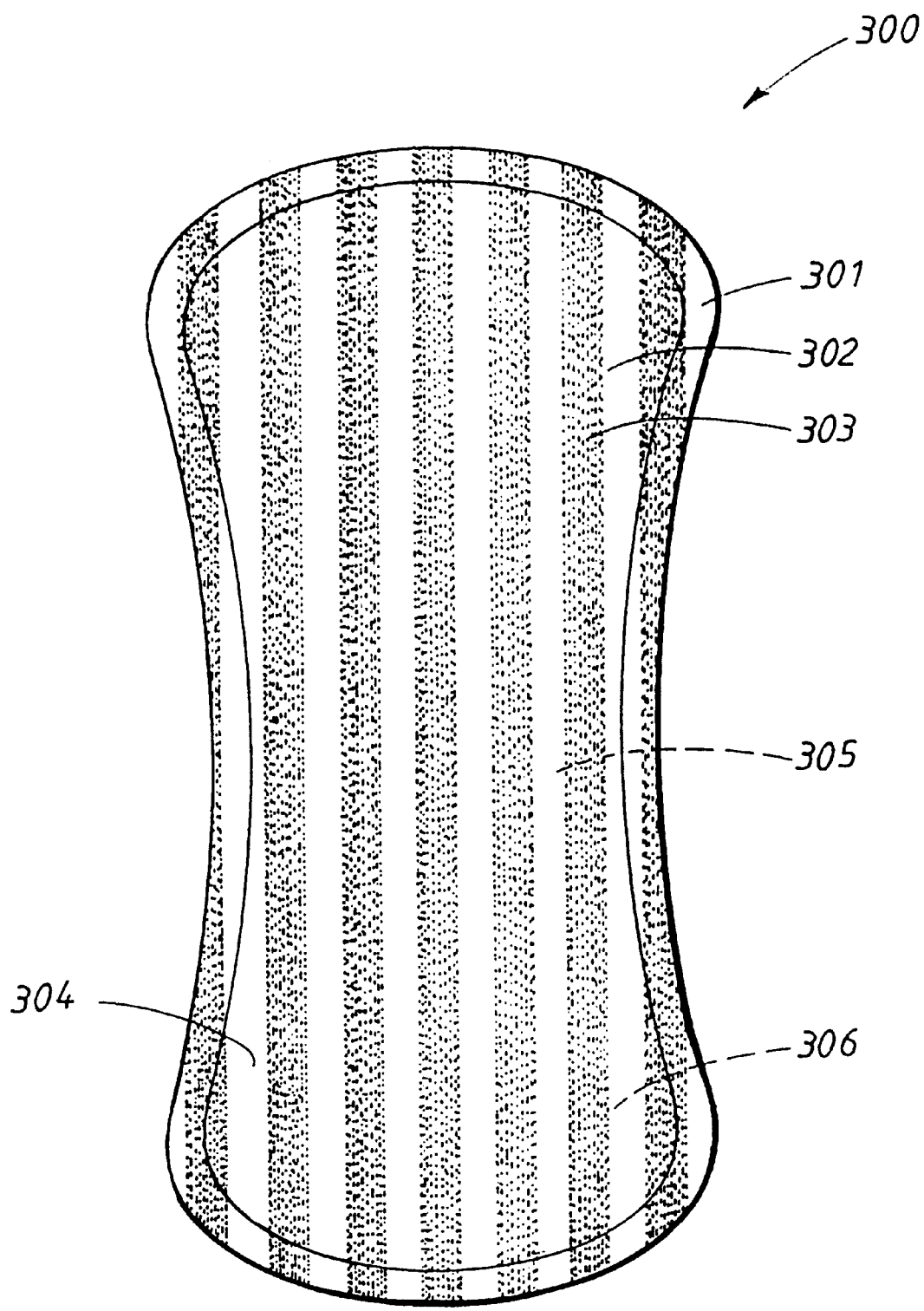

The sanitary napkin 300 shown in FIG. 3 comprises a liquid-pervious cover layer 301 according to the invention, a liquid-impervious cover layer 305, and an absorbent body 306 enclosed between the cover layers. The liquid-impervious cover layer 305 comprises a plastic film, a hydrophobicated fibre fabric, a laminate of these materials, or any other similar material suitable for the use, placed on the side of the sanitary napkin which is intended to be facing away from the user during use.

The absorbent body 306 enclosed between the cover layers 301, 305 is usually composed of one or several layers of cellulose fluff pulp. The cellulose fluff pulp may be blended with fibres or particles of a highly absorbent polymeric material of the type which during absorption chemically binds large quantities of liquid while forming a liquid-containing gel. In order to improve the properties of the absorbent body 306, additional components may further be included in the absorbent body. Examples of such components are binder fibres, shape-stabilizing components, or the like. Furthermore, the absorbent body 306 can be constituted of absorbent foams, or of any other liquid-absorbent material.

The cover layers 301, 305 have a larger extension in the plane of the sanitary napkin 300 than the absorbent body 306, around the entire periphery of this. The projecting portions 308 of the cover layers 301, 305 are mutually connected around the absorbent body 306, for example by means of gluing, welding, or in another way.

The liquid-pervious cover layer 301 has a similar construction to the liquid-pervious cover layer 1 shown in FIG. 1 and, accordingly, exhibits a carrier layer 302, to which fibres 303 are attached in a surface pattern of stripes or band-shaped regions alternating with fibre-free, or essentially fibre-free band-shaped regions 304. The width of the fibre-free regions 4 should be in the order of 3–15 mm and preferably 3–10 mm.

The fibres 303 are attached to the carrier layer 302 with an attachment angle α which is approximately 90°, but which of course may vary somewhat between the different fibres. The cover layer 301 is liquid-pervious since the carrier layer 302 exhibits perforations though the material, or by means of the carrier layer being constituted of a liquid-pervious material such as for example a hydrophilic nonwoven. Furthermore, the absorbent body 306 can constitute a carrier layer 302, when it exhibits a sufficient cohesive ability, wherein the fibres are attached directly to the side of the absorbent structure which is intended to bear against the user during use.

In the preceding embodiments, the invention has been described with reference to sanitary napkins but is, as already mentioned, of course also applicable to incontinence protectors, diapers, panty-liners and the like.

The invention further relates to all conceivable combinations of the above-mentioned embodiments, and is also applicable for other embodiments within the scope of the following claims.

What is claimed is:

1. A liquid-pervious cover layer for an absorbent article selected from the group consisting of a diaper, an incontinence protector, and a sanitary napkin, which comprises:

a liquid-pervious carrier layer having a first surface and a second surface; said first surface of the carrier layer comprising a multitude of individually arranged fibers; each fiber having a first fiber end and a second fiber end, and being attached with one fiber end against the first surface of the carrier layer; said carrier layer comprising a plurality of regions which are substantially free from fibers and which each occupies a surface such that a circle having a diameter of 3 to 15 mm can be accommodated within each fiber-free region.

2. The liquid-pervious cover layer according to claim 2, wherein each fiber-free region occupies a surface such that a circle having a diameter of 3 to 10 mm can be accommodated within each fiber-free region.

3. The liquid-pervious cover layer according to claim 1, wherein the individual fibers comprise bicomponent fibers exhibiting a fiber surface and a core, and wherein at least the fiber surface is hydrophobic.

4. The liquid-pervious cover layer according to claim 3, wherein the fiber surface is more hydrophobic than the core.

5. The liquid-pervious cover layer according to claim 3, wherein the fiber surface has a lower melting temperature than the core.

6. The liquid-pervious cover layer according to claim 1, wherein the fibers comprise hollow fibers having an outer surface and an inner surface, and at least the outer surface is hydrophobic.

7. The liquid-pervious cover layer according to claim 1, wherein the fibers are attached to the first surface of the carrier layer with an attachment angle α between the carrier layer and each individual fiber ranging from 30–90°.

8. The liquid-pervious cover layer according to claim 1, wherein the carrier layer comprises a multilayered laminate.

9. The liquid-pervious cover layer according to claim 1, wherein the carrier layer comprises a perforated plastic film.

10. The liquid-pervious cover layer according to claim 1, wherein the carrier layer comprises a hydrophilic nonwoven.

11. The liquid-pervious cover layer according to claim 1, wherein the carrier layer, within different regions of the surface of the carrier layer, exhibits a difference in the number of attached individual fibers per unit of area.

12. The liquid-pervious cover layer according to claim 1, wherein the fibers are hydrophobic and 0.3–2.5 mm long.

13. The liquid-pervious cover layer according to claim 12, wherein the hydrophobic fibers are 0.3–1.5 mm long.

14. The liquid-pervious cover layer according to claim 1, wherein the carrier layer comprises a plurality of fibers arranged in band-shaped regions on the first surface of the carrier layer, and the distance between two neighboring fiber-covered regions ranges from 3–15 mm.

15. The liquid-pervious cover layer according to claim 14, wherein the distance between two neighboring fiber-covered regions ranges from 3–10 mm.

16. The liquid-pervious cover layer according to claim 1, wherein the fiber-free regions occupy at least 25% of the surface of the carrier layer.

17. An absorbent article selected from the group consisting of a diaper, an incontinence protector and a sanitary napkin, comprising an absorbent body enclosed in a cover, wherein at least a portion of the cover consists of a liquid-pervious cover layer comprising a carrier layer against which individual hydrophobic fibers detached from each other and each having two fiber ends, are attached with one fiber end against the carrier layer with an attachment angle α between the carrier layer and each individual fiber; said carrier layer comprising a plurality of regions which are substantially free from fibers and which each occupies a surface such that a circle having a diameter of 3 to 15 mm can be accommodated within each fiber-free region of the carrier layer.

18. The absorbent article according to claim 17, wherein each fiber-free region occupies a surface such that a circle having a diameter of 3 to 10 mm can be accommodated within each fiber-free region of the carrier layer.

19. A method of manufacturing a cover layer for an absorbent article, which comprises:

providing a liquid-pervious carrier layer;

providing a plurality of individual fibers each having a first fiber end and a second fiber end;

applying the first fiber end against the carrier layer;

wherein the fibers, at least at the first fiber end, in cross-section comprise a first portion primarily consisting of a first component, and a second portion primarily consisting of a second component, at least the first component being fusible and having a melting temperature at which the second component occurs in a solid state;

causing only the first component to melt, at least at the first fiber end of the fibers, whereby the fibers attach to the carrier layer; and lowering the temperature of the fibers to a temperature below the melting temperature of the first component so as to obtain a solid connection between the fibers and the carrier layer; said fibers being arranged in spaced apart regions with fiber-free regions therebetween, each fiber-free region occupying a surface such that a circle having a diameter of 3 to 15 mm can be accommodated in each fiber-free region.

* * * * *